United States Patent
Chen et al.

(10) Patent No.: US 12,020,782 B1
(45) Date of Patent: Jun. 25, 2024

(54) OOCYTE QUALITY ANALYSIS SYSTEM

(71) Applicant: Inti Taiwan, Inc., Zhubei (TW)

(72) Inventors: Wei-Ming Chen, Zhubei (TW);
I-Chiao Hsieh, Zhubei (TW);
Chung-Li Chiang, Zhubei (TW)

(73) Assignee: Inti Taiwan, Inc., Zhubei (TW)

( * ) Notice: Subject to any disclaimer, the term of this patent is extended or adjusted under 35 U.S.C. 154(b) by 0 days.

(21) Appl. No.: 18/189,683

(22) Filed: Mar. 24, 2023

(51) Int. Cl.
*G16C 20/70* (2019.01)
*G16B 5/00* (2019.01)
*G16B 40/00* (2019.01)
*G16H 30/20* (2018.01)

(52) U.S. Cl.
CPC ............... *G16C 20/70* (2019.02); *G16B 5/00* (2019.02); *G16B 40/00* (2019.02); *G16H 30/20* (2018.01)

(58) Field of Classification Search
CPC .......... G16C 20/70; G16B 5/00; G16B 40/00; G16H 30/20
See application file for complete search history.

(56) References Cited

U.S. PATENT DOCUMENTS

| | | |
|---|---|---|
| 2013/0184518 A1 | 7/2013 | Zarnescu et al. |
| 2019/0042958 A1 | 2/2019 | Letterie et al. |

FOREIGN PATENT DOCUMENTS

| | | | |
|---|---|---|---|
| CN | 110969616 A | | 4/2020 |

OTHER PUBLICATIONS

Isa et al. (Appl. Sci. (2023) vol. 13, 22 pages; published Jan. 16, 2023).*
Ma et al. (Theranostics (2021) vol. 11, Issue 15:7391-7424).*
Liu et al. Micromachines (2019) vol. 10: 16 pages).*
Lamont et al. (Journal of the Mechanical Behavior of Biomedical Materials (2023) vol. 138:12 pages).*
McQuin et al. (PLoS Biology (2018) vol. 16(7):17 pages).*
Gröger et al. at pp. 65-75 (Medical Image Learning with Limited and Noisy Data (2022), LNCS 13559; article entitled: BoxShrink: From Bounding Boxes to Segmentation Masks by Gröger et al. at pp. 65-75).*
Moen et al. (Nature Methods (2019) vol. 16:1233-1246).*
Khalilian et al., "Estimating Young's modulus of zona pellucida by micropipette aspiration in combination with theoretical models of ovum," Journal of Royal Society Interface, 2010, 7, p. 687-694, doi:10.1098/rsif.2009.0380.
Yanez et al., "Human oocyte developmental potential is predicted by mechanical properties withinhours after fertilization," Nature Communications, 2017,7:10809, pp. 1-12, DOI: 10.1038/ncomms10809.
International Search Report and Written Opinion mailed Dec. 6, 2023 in International Application PCT/CN2023/108002.

* cited by examiner

*Primary Examiner* — Lori A. Clow
(74) *Attorney, Agent, or Firm* — Knobbe, Martens, Olson & Bear, LLP

(57) ABSTRACT

The present disclosure generally relates to systems and methods for evaluating viability of oocytes. In some implementation examples, an image sequence associated with an oocyte being aspirated into a pressure tool is obtained. Based on the image sequence and pressures applied on the oocyte, morphological features and mechanical features associated with the oocyte can be derived. At least some of the features can then be fed into a machine learning model to determine metrics indicative of quality of the oocyte, where a particular metric may be indicative of blastocyst formation. Optionally, the determined oocyte quality information can be presented to a user via an interactive user interface.

31 Claims, 9 Drawing Sheets

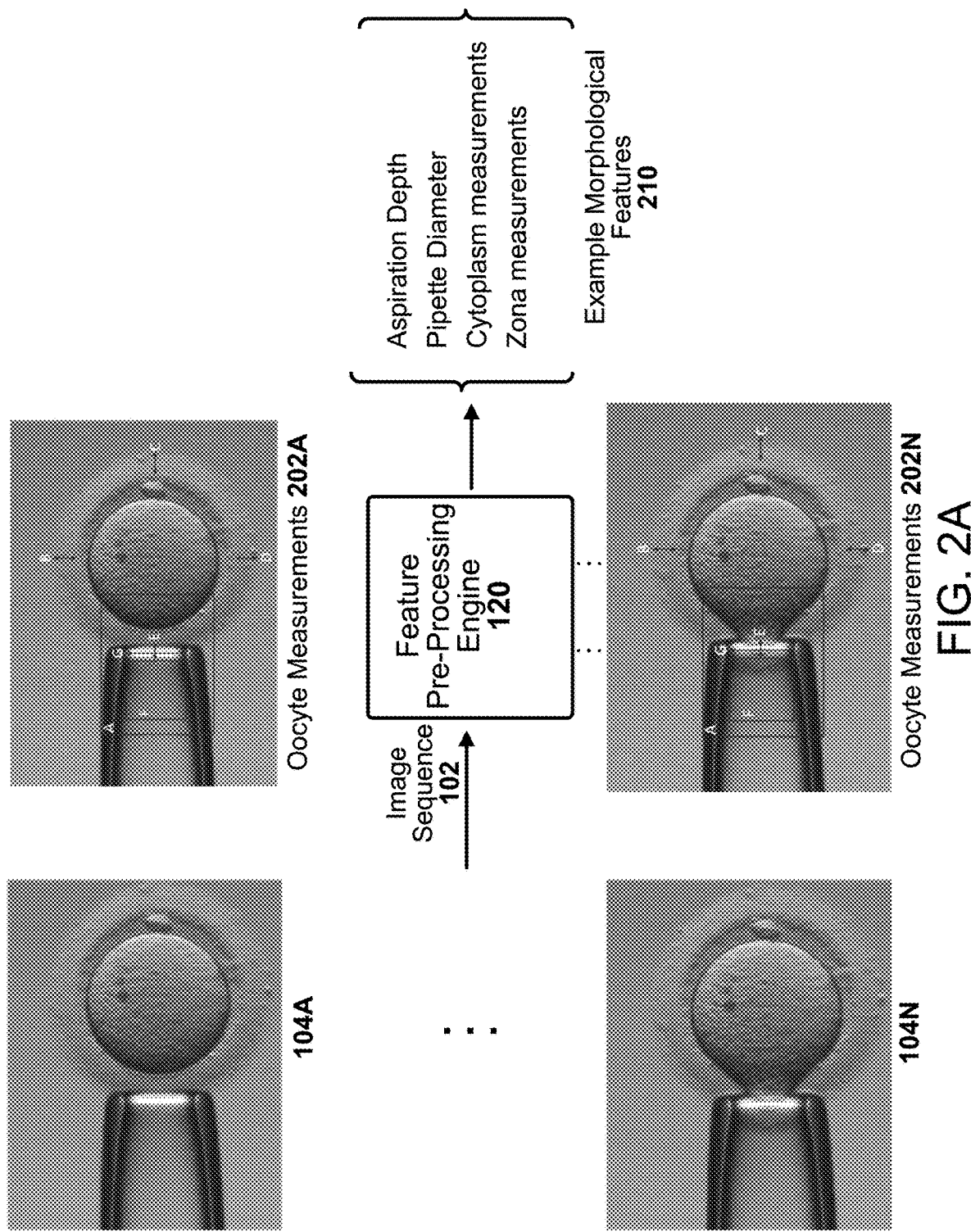

US 12,020,782 B1

OOCYTE QUALITY ANALYSIS SYSTEM

FIELD OF THE DISCLOSURE

The present disclosure relates to medical analysis using machine learning models, and more particularly, to analyzing oocytes using sensor information and machine learning models.

BACKGROUND

In recent years, there have been advancements in treatments for infertility. An example treatment includes in-vitro-fertilization ("IVF"). An IVF starts with an ovarian stimulation phase which stimulates egg production. Eggs (oocytes) may be retrieved from the patient and fertilized in-vitro to form embryos. Multiple tests and analysis may be performed on the embryos in an effort to select the most viable and/or advantageous embryo for implantation. However, such tests and analyses suffer from technological problems and thus an accurate scheme to effectuate this selection presents technological challenges.

As an example, different grading systems have been developed to assist in determining the viability of each embryo. These grading systems generally involve manual annotation of embryo image or time-lapse video. As may be appreciated, the selection process proves to be error-prone due to, for example, the subjective judgments of embryologists. Additionally, there is currently no standard grading system that is universally adopted to select quality oocytes. Current automated techniques which leverage analyses of embryos are inaccurate and fail to utilize disparate sensor information.

BRIEF DESCRIPTION OF THE DRAWINGS

FIG. 2A illustrates example morphological features of an oocyte generated by the feature pre-processing engine of FIG. 1.

DETAILED DESCRIPTION

Figure 1:
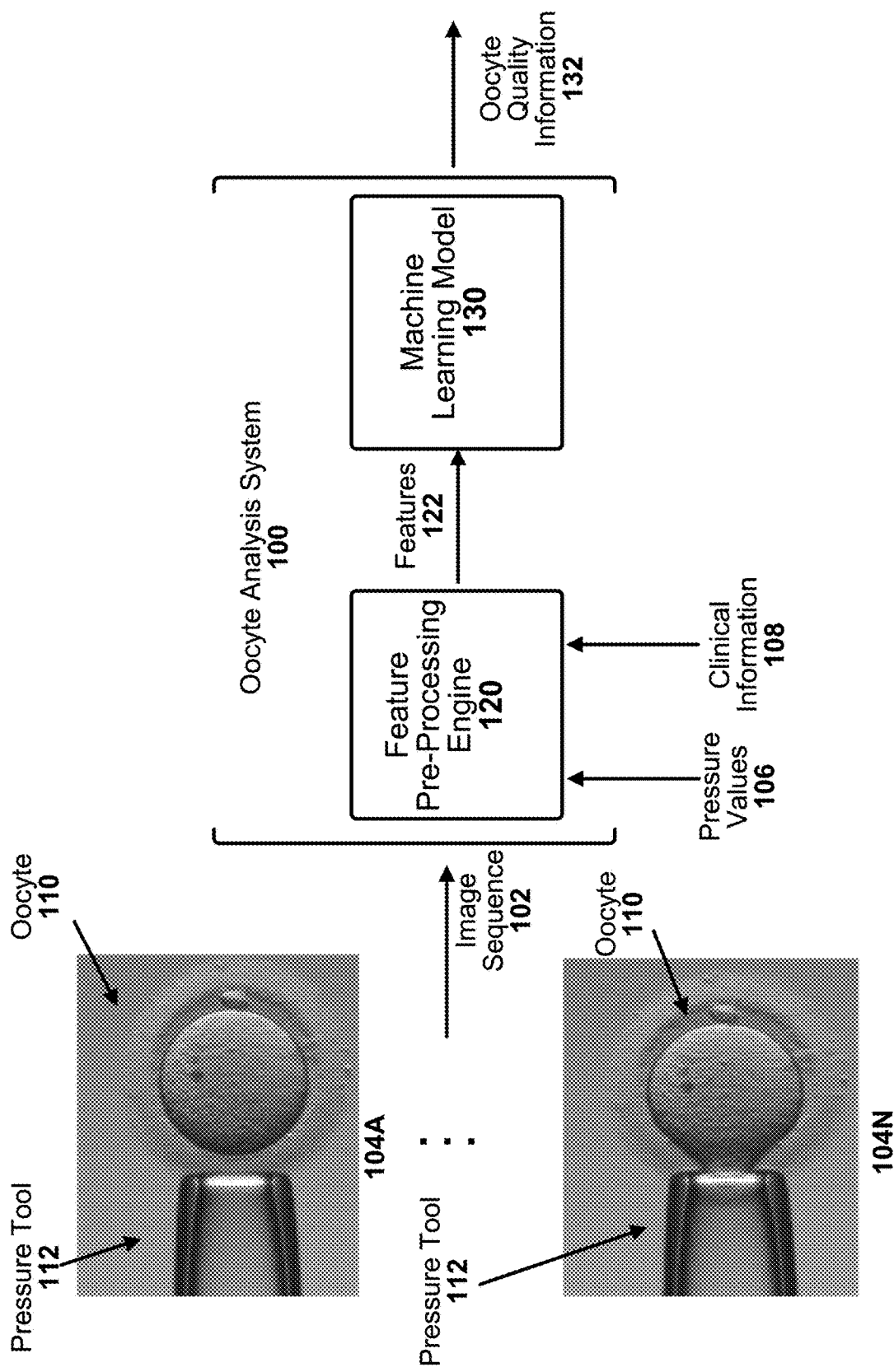
FIG. 1 is a block diagram of an example oocyte analysis system which includes a feature pre-processing engine and a machine learning model in accordance with some embodiments of the present disclosure.

This specification describes techniques for selecting good quality eggs (e.g., oocytes) which have, for example, an enhanced probability of blastocyst formation. As will be described, a system may leverage disparate sensor information to analyze oocytes using machine learning techniques. The sensor information may include, for example, images of the oocytes (unfertilized eggs) undergoing deformation due to application of pressure along with pressure measurements indicative of the pressure applied to the oocytes. This sensor information may enable an understanding of the morphological and mechanical characteristics of the oocytes as the oocytes undergo deformation, which allows for a more accurate assessment of the quality of each oocyte. In contrast, prior techniques relied upon hand-tuned models or grading systems which used a single type of information (e.g., images) and which were prone to error. As will be described, the disclosed technology leverages the disparate sensor information, along with specifically trained models, to more accurately and efficiently assess qualities or viability of eggs at an earlier stage.

To evaluate the viability of eggs, some prior techniques rely upon an embryologist to visually assess embryos (e.g., fertilized eggs). Some clinics record images of the embryos, and an embryologist may score an embryo based on various grading systems and their visual assessment. One major challenge in embryo selection is the high level of labor, subjectivity and variability that exists between embryologists of different skill levels and grading systems of different performances. Specifically, embryologists often disagree with each other or even with themselves on which embryo has the best viability for transfer after assessing embryos visually for considerable amount of time. Further, it remains unclear which embryonic features associated with a particular grading system are ultimately predictive on the success rate of each embryo.

Other prior techniques include automated techniques for selecting quality eggs. These techniques may rely on particular characteristics of fertilized eggs. Typically, the particular characteristics of fertilized eggs are obtained by analyzing (e.g., using microscopes and computer vision technology) video capturing changes in eggs during growth and development. However, selecting eggs based on these characteristics (e.g., characteristics derived based on observing the growth and development of eggs) may not yield satisfactory results.

In contrast, the disclosed technology allows for analyzing the viability of eggs at an earlier stage (e.g., when eggs are still unfertilized rather than when eggs are fertilized). Thus, the disclosed technology can eliminate the extra complexity associated with fertilizing eggs which may not be implanted later. By utilizing machine learning models for selecting oocytes based on extracted features of the oocytes, the disclosed technologies can obtain more objective and quantitative analysis on the viability of the oocytes.

Furthermore, the disclosed technology leverages machine learning techniques to analyze both morphological and mechanical features of oocytes. The morphological features, as will be described, can include geometrical information associated with an oocyte such as the size or length of zona pellucida, cytoplasm, polar body, perivitelline space, extents to which the oocyte is aspirated into a pressure-applying tool (e.g., aspiration depth), and so on. The mechanical features, as will be described, can include parameters determined or derived based on deformation characteristics of an oocyte. For example, mechanical features can include at least morpho-kinetic parameters described in a particular model (e.g., Zener model) or the like.

These machine learning techniques may utilize the features to indicate one or more metrics indicative of quality of an oocyte. An example metric may include a value indicative of a likelihood or probability of blastocyst formation. Additional example metrics may include an indication of the oocyte being "good", the likelihood or probability of aneuploidy and implantation rate, and so on.

More specifically, the system may obtain an image sequence which depicts an oocyte being deformed due to a mechanical stimulus. An example stimulus may include the oocyte being aspirated into a portion of a pressure tool (e.g., a pipette) which applies pressure to the oocyte. The system may use example computer vision techniques to process the image sequence to derive the above-described morphological features and mechanical features. In some examples, to deal with different resolutions of hardware (e.g., microscope cameras) which are used to capture images, a normalization technique may be utilized. The normalization technique may be integrated as a part of image processing techniques performed on captured image sequences associated with oocytes. The normalization technique will be described in greater detail below.

The extracted morphological features and mechanical features of the oocyte may then be used to train, or run inferences using, a machine learning model. The training process may include using a subset of the morphological and mechanical features to train the machine learning model. The trained machine learning model may then be employed to generate one or more metrics indicative of the quality of the oocyte, where a particular metric may be indicative of blastocyst formation from the oocyte.

Additionally, and optionally, the metrics may be presented to a user or a professional (e.g., an embryologist) through an interactive user interface. As such, further analysis or evaluation on the viability of the oocyte may be more efficiently conducted. Thus, more objective, automated and time-efficient evaluation of the viability of oocytes can be achieved based on embodiments of the present disclosure.

As an example, accuracy associated with the disclosed technology, a total of 185 oocytes were evaluated to assess their viability of blastocyst formation. The 185 samples were split by 80% for training a machine learning model and 20% for testing the machine learning model. The machine learning utilized for viability evaluation was a Support Vector Machine (SVM). The machine learning model was trained to predict whether there will be blastocyst or no blastocyst for a particular oocyte in the samples. The predictive outcomes were statistically analyzed and showed an accuracy of 73%, a sensitivity of 85%, a specificity of 59%, a positive predictive value (PPV) of 77%, and a negative predictive value (NPV) of 71%. Compared with statistics compiled based on prediction made by an embryologist that show an accuracy of 45%, a sensitivity of 59%, a specificity of 33%, a PPV of 43%, and a NPV of 49%, the systems and methods according to the present disclosure achieve a better performance statistically.

The foregoing aspects and many of the attendant advantages of this disclosure will become more readily appreciated as the same become better understood by reference to the following description, when taken in conjunction with the accompanying drawings.

Example Block Diagrams

FIG. 1 is a block diagram of an example oocyte analysis system 100 which includes a feature pre-processing engine 120 and a machine learning model 130 in accordance with some embodiments of the present disclosure. As illustrated, the feature pre-processing engine 120 may receive an image sequence 102 of an oocyte (e.g., a mammalian oocyte, such as a human oocyte), pressure values 106 and clinical information 108 as inputs. The feature pre-processing engine 120 may then generate features 122 associated with the oocyte as outputs. The features 122 can be input into the machine learning model 130, which outputs oocyte quality information 132. The oocyte quality information 132 can be presented to a user for further analysis.

The image sequence 102 may include multiple images (e.g., images 104A-104N), for which each image depicts an oocyte 110 along with a pressure tool 112. More specifically, images 104A-104N may form a video depicting a process of aspirating the oocyte 110 into the pressure tool 112. Image 104A can represent, for example, the first frame of the video and image 104N can represent, for example, the last frame of the video. Image 104A depicts the oocyte 110 as not yet being aspirated into the pressure tool 112 while image 104N depicts at least part of the oocyte 110 being aspirated into the pressure tool 112. In some examples, the image sequence 102 may have a frame rate of 10 Hz, 20 Hz, 70 Hz, 3000 Hz, with a total video length of 1 second, 2 seconds, 10 seconds, and so on.

Additionally, in some embodiments, the pressure tool 112 is a pipette that has a diameter between particular thresholds (e.g., between 10 micrometer (μm), 20 μm, 40 μm, and 60 μm, 70 μm, 100 μm, and so on). The pipette may apply a negative pressure (e.g., a lower pressure inside the pipette relative to the pressure outside the pipette) on the oocyte 110 for aspirating the oocyte 110 into the pipette without damaging the oocyte 110. An example pressure may include between −0.01 psi to −0.5 psi. For example, the pipette may abut or otherwise be in contact with the oocyte. Although the image sequence 102 illustrates the oocyte 110 being aspirated into the pressure tool 112, in some embodiments the pressure tool 112 may apply other forms of mechanical stimulus (e.g., positive pressure). In this way, different morphological responses of the oocyte 110 may be obtained. The morphological responses can be used by the feature pre-processing engine 120 to analyze and/or extract different morphological features.

In FIG. 1, the feature pre-processing engine 120 is illustrated as using the image sequence 102, pressure values 106, and clinical information 108 to output features 122 associated with the oocyte 110. In some embodiments, all of this information may be utilized to determine features 122. In some embodiments, a subset of the information may be used.

With respect to pressure values 106, the pressure values 106 can include a plurality of numerical values that indicate how much force is applied on the oocyte 110 during the timeframe or time period of the images 104A-104N. For example, the pressure values 106 may indicate that a first pressure (e.g., −0.3 psi) is applied on the oocyte 110 at the moment (e.g. time or timestamp) image 104A was captured and a Nth pressure is applied on the oocyte 110 at the moment the image 104N was captured. The pressure values applied on the oocyte 110 at different images in the image sequence 102 may be the same or may not be the same.

In some examples, the pressures applied on the oocyte 110 may be increasing as time progresses while in other examples the pressures applied may be decreasing as time progresses. Additionally, the pressure values 106 may include forces applied on the oocyte 110, where the forces can be calculated based on pressures generated by the pressure tool 112 and applied on the oocyte 110. The forces applied on the oocyte 110 can be used to derive mechanical features of the oocyte 110, which will be described in greater detail later with respect to FIG. 2B.

The clinical information 108 may include age and body mass index (BMI) of the patient from whom the oocyte 110 originates. Additionally, the clinical information 108 may include information indicating whether the oocyte 110 has gone through cryopreservation (CP). The clinical information 108 may also indicate available number of mature oocyte (MII) associated with the patient.

Based on at least some of the image sequence 102, pressure values 106 and clinical information 108, the feature pre-processing engine 120 may extract the features 122 associated with the oocyte 110. The features 122 can include morphological features (sizes or lengths of zona pellucida, cytoplasm, polar body, or perivitelline space) and mechanical features (e.g., elasticity and/or viscosity) of the oocyte 110. Certain features may be generated per image in the image sequence 102, while other features may be determined based on all, or a subset of, the images. These features 122 will be described in more detail below, with respect to FIGS. 2A-2B.

Based on the features 122, the machine learning model 130 may generate oocyte quality information 132 for the oocyte 110. Example information 132 may include the likelihood of blastocyst formation. In some embodiments, the machine learning model 130 may be a support vector machine (SVM) which is trained to output the information 132. In other examples, the machine learning model 130 may be a deep learning model. For example, the deep learning model may include a recurrent neural network (RNN) which is trained to output the information 132. In this example, the RNN may be input the features 122 as a sequence and may output the information 132 for the sequence. The model may also be a convolutional neural network or fully-connected network. The machine learning model 130 may utilize all or a subset of the features 122 to determine the oocyte quality information 132. For example, the SVM may be trained to utilize a subset of the features 122.

In some embodiments, the oocyte quality information 132 may further indicate the likelihood of whether a "usable" blastocyst will be formed by the oocyte 110, where "usable" means the blastocyst formed by the oocyte 110 can be suitable for transferring or for implantation. Additionally, or alternatively, the oocyte quality information 132 may indicate the likelihood of whether the blastocyst to be formed by the oocyte 110 will be "unusable" blastocyst, where "unusable" means the blastocyst formed by the oocyte 110 will be in such poor condition that the blastocyst is not suitable for furthering an IVF treatment.

Block Diagram—Morphological Feature Generation

FIG. 2A illustrates example morphological features of an oocyte generated by the feature pre-processing engine 120. The example morphological features 210 may form part of the features 122 of FIG. 1. The example morphological features 210 may include aspiration depth of the oocyte 110, the diameter of the pressure tool 112 (e.g., a pipette), the size and/or shape of the cytoplasm and zona pellucida of the oocyte 110, and so on. Optionally, these features may be determined for each input image.

The determination of some of the example morphological features 210 of the oocyte 110 can be illustrated by the oocyte measurements 202N, which depicts example measurements (e.g., bounding box A, distance B, distance C, distance D, distance E, bounding box F, and distance G). The oocyte measurements 202N corresponds to the measurement of the image 104N, and the oocyte measurements 202A corresponds to the measurement of the image 104A.

With respect to the illustrated oocyte measurements 202N, bounding box A may represent a region of interest (ROI) which is cropped for further image processing performed on the image sequence 102. Distance B may indicate a length and/or size of an upper side of the zona pellucida of the oocyte 110. Distance C may indicate a length and/or size of a right side of the zona pellucida of the oocyte 110. Distance D may indicate a length and/or size of a lower side of the zona pellucida of the oocyte 110. Distance E may indicate the inner zona pellucida of the oocyte 110. Distance G may indicate a length of the inner diameter of the pressure tool 112. Bounding box F may represent a region of interest (ROI) which may be cropped for calculating the aspiration depth of the oocyte 110 into the pressure tool 112. Calculating aspiration depth is described in more detail below.

Different image processing and object identification techniques may be utilized to obtain the example morphological features 210. In some examples, computer vision techniques can be used to derive the example morphological features 210. For example, edge detection techniques may be used to identify boundaries associated with the different portions of the oocyte. In other examples, image segmentation models based on deep learning algorithms can be utilized to derive the example morphological features 210. For example, segmentation masks may be generated for the features 210. As may be appreciated, a segmentation mask may assign a color or pixel value indicative of whether a pixel forms part of a classified feature (e.g., zona pellucida and so on). The derivation of each of the example morphological features are discussed with greater detail below.

Bounding box A can define the ROI that will be cropped for any image (e.g., image 104A or image 104N) of the image sequence 102, where some of the morphological features 210 such as the inner boundary of the zona pellucida, the size of the pressure tool 112 and the aspiration depth of the oocyte 110 can be calculated within this ROI. In some examples, bounding box A can be identified according to the following example technique. For example, a tip of the pressure tool 112 (e.g., a pipette) which contacts the oocyte 110 can be identified and/or positioned based on a pipette tip image that may be obtained in advance. Based on the position of the tip of pipette, the bounding box A can be drawn to make out the ROI around the tip of pipette. Although bounding box A is shown as a rectangular, other shapes can be used to define the ROI.

Distance B, distance C and distance D define the length or thickness of the zona pellucida on the upper side, right side and lower side, respectively. By averaging the lengths of these distances, a morphological feature which is indicative of an average size of the zona pellucida of the oocyte 110 may be obtained. Additionally, distance E may be defined based on the position of the tip of pipette that is obtained above when demarcating bounding box A and the inner boundary of the zona pellucida of the oocyte 110.

As an example, distance E can be useful for deriving a horizontal (e.g., along the direction of arrow C and arrow E) length of the cytoplasm of the oocyte 110. More specifically, the horizontal length of the cytoplasm of the oocyte 110 can be derived by subtracting the combined length of arrow E and arrow C from the horizontal length (e.g., defined by the right tip of arrow C and left tip of arrow E) of the oocyte 110. The horizontal length of the cytoplasm of the oocyte 110 can also be utilized as a part of the example morphological features 210. Similarly, the vertical (e.g., along the direction of arrow B and arrow D) length of the cytoplasm of the oocyte 110 can be derived by subtracting the combined length of arrow B and arrow D from the vertical length (e.g., defined by the top end of arrow B and bottom end of arrow D) of the oocyte 110. The vertical length of the cytoplasm of the oocyte 110 can also be used as a part of the features 122.

The bounding box F can be utilized as a ROI for calculating the aspiration depth (e.g., how much length the oocyte 110 is aspirated into the pressure tool 112 compared with the position of the oocyte 110 right before being aspirated) of the oocyte 110. The aspiration depth may be useful for deriving mechanical features associated with the oocyte 110, which is discussed in more detail below with respect to FIG. 2B. In some embodiments, the aspiration depth can be derived by determining the deepest horizontal position (e.g., end of aspiration depth) into the pressure tool 112 the oocyte 110 is aspirated. The distance between the end of aspiration depth and the inner boundary of the zona pellucida of the oocyte 110 may then be calculated. Below is an example technique for determining aspiration depth.

The ROI (e.g., bounding box F) may be demarcated (e.g., identified) based on the position of the tip of the pressure tool 112 which is in contact with the oocyte 110. As illustrated in the oocyte measurements 202N, the bounding box F has a rectangular shape; however, in other examples, the bounding box F can be of different shapes (e.g., square or irregular shapes). In some embodiments, the bounding box F extends to the left-most part of an image at a particular threshold distance. That is, the distance may be set to ensure that it encompasses an end or extremity of the oocyte being aspirated into the tool 112.

Pixels which are aligned with each other vertically within the bounding box F may be summed to derive a pixel curve. More specifically, assuming the bounding box F spans across N pixels horizontally and M pixels vertically, the pixel intensities of the pixels having the same horizontal position within the bounding box F can be summed. For example, M pixels may be summed at a particular horizontal position. Thus, N may be a positive integer which depends on the resolution of the image sequence 102 and the horizontal length of the bounding box F. For example, if there are 50 horizontal positions then for each position the pixels which extend vertically within the box F may be summed to arrive at a value.

These values may then be used to generate a pixel curve which has the summed values on a first axis (e.g., the y axis) and the number of horizontal positions on a second axis (e.g., the x axis). The pixel curve may be smoothed using signal processing techniques such as sliding window moving average method.

Subsequently, the first order derivative may be determined on the smoothed pixel curve. This derivative may represent vertically summed intensities. The minimum value of the derivative of the pixel curve may then be found, which indicates the end of aspiration depth of the oocyte 110 for a particular image (e.g., image 104A).

The above-described example technique may be performed on other images in the image sequence 102 such that the end of aspiration depth can be acquired for each of the images 104A-104N. In some examples, the aspiration depth can be calculated based on the end of the aspiration depth and an inner boundary of zona pellucida of the oocyte 110. By calculating the aspiration depth for each of the images 104A-104N in the image sequence 102, the aspiration depth of the oocyte 110 over time can be plotted as a chart where a first axis shows the time, and a second axis shows the aspiration depth of the oocyte 110. In some examples, the aspiration depth can be further normalized based on the size of zona pellucida of the oocyte 110. For example, the aspiration depth can be normalized by subtracting the average of distance B, distance C and distance D from the calculated aspiration depth.

While the above describes an example of determining aspiration depth, as may be appreciated other techniques may be used and fall within the disclosure herein. For example, deep learning techniques may be used to determine a boundary or extremity of the oocyte into the tool. As another example, edge detection techniques (e.g., edge detection kernels) may be used to identify the edge of the oocyte in the tool.

Additionally, and optionally, the feature pre-processing engine 120 may not need to analyze all the images in the image sequence 102. In some examples, only a portion of the image sequence 102 is analyzed by selecting a start frame and performing analysis on the start frame and the frames after the start frame. The start frame may be the frame that captures the image of the oocyte 110 right before the oocyte 110 was to be aspirated into the pressure tool 112. For example, the system may identify the frame associated with a time stamp prior to a time or time stamp associated with application of negative pressure. As another example, the system may analyze the image frames and identify a frame prior to one which has an aspiration depth greater than a threshold (e.g., zero, a small value, and so on). Advantageously, the analysis can be more time-efficient and consuming less amount of computing power.

Additionally, and optionally, the pre-processing engine 120 can reduce (e.g., shrink) the number of frames to be analyzed by removing consecutive frames during which the oocyte 110 remains still or unmoved. For example, the pre-processing engine 120 may determine that only 0.5 seconds of the video depicted by the image sequence 102 show movement of the oocyte 110 while the remaining 1.5 seconds of the video of the image sequence 102 show the oocyte 110 remains unmoved or stays relatively static. The pre-processing engine 120 may then extract the 0.5 seconds of the video for further analysis. Advantageously, the analysis time can be reduced by shrinking the video length for analysis.

The feature pre-processing engine 120 can additionally determine the inner diameter of the pressure tool 112, which is illustrated by distance G in the oocyte measurements 202N. In some embodiments, the length of the inner diameter of the pressure tool 112 can be acquired by calculating the number of pixels that are aligned vertically along the inner diameter of the pressure tool 112. The inner diameter of the pressure tool 112 can be used as a normalization factor for increasing the interoperability of the oocyte analysis system 100 across different video capturing platforms that might have different hardware specifications (e.g., resolutions of captured images).

Normalization may additionally relate to the oocyte's z-height in an object housing the oocyte while images are being taken. That is, the oocyte may be placed in water or another liquid and vary in height (e.g., closer to the bottom of the water or the top). This adjustment in height may therefore change dimensions of the oocyte as compared to another oocyte or as compared to the same oocyte in different images in the sequence 102. For example, the oocyte may have slight changes in height during the image sequence 102.

More specifically, the aspiration depth of an oocyte over time may be normalized by a ratio between an inner diameter of the pressure tool 112 and a pixel length of a particular image sequence. Using computer vision techniques, an inner diameter of the pressure tool 112 can be identified and the length of the inner diameter can then be calculated by counting how many pixels along an-axis of the pressure tool 112 the inner diameter covers. For example, the inner diameter of the pressure tool 112 may span across 1,000 pixels and the aspiration depth can then be divided by 1,000 for normalization. Normalizing the aspiration depth of oocytes by the inner diameter of the pressure tool 112 can put the different frames of oocytes acquired under different image capturing settings on the same footing for the purpose of calculating morphological features associated with oocytes. As such, the inter-operability and reproducibility of the presently disclosed systems and methods can be enhanced.

Additional morphological features associated with the oocyte 110 can also be acquired by the feature pre-processing engine 120. Example features may include sizes and/or lengths of the polar body, cytoplasm and/or perivitelline space (e.g., PVS, the space between zona pellucida and cytoplasm) of the oocyte 110. Both image segmentation models based on deep learning algorithms and computer vision technology can be adopted to determine these additional morphological features. Advantageously, the additionally morphological features available can be potentially useful for training and/or testing the machine learning model 130 to improve the accuracy, sensitivity, specificity, NPV, and PPV of the results generated by the machine learning model 130.

Block Diagram—Mechanical Feature Generation

Figure 2B:
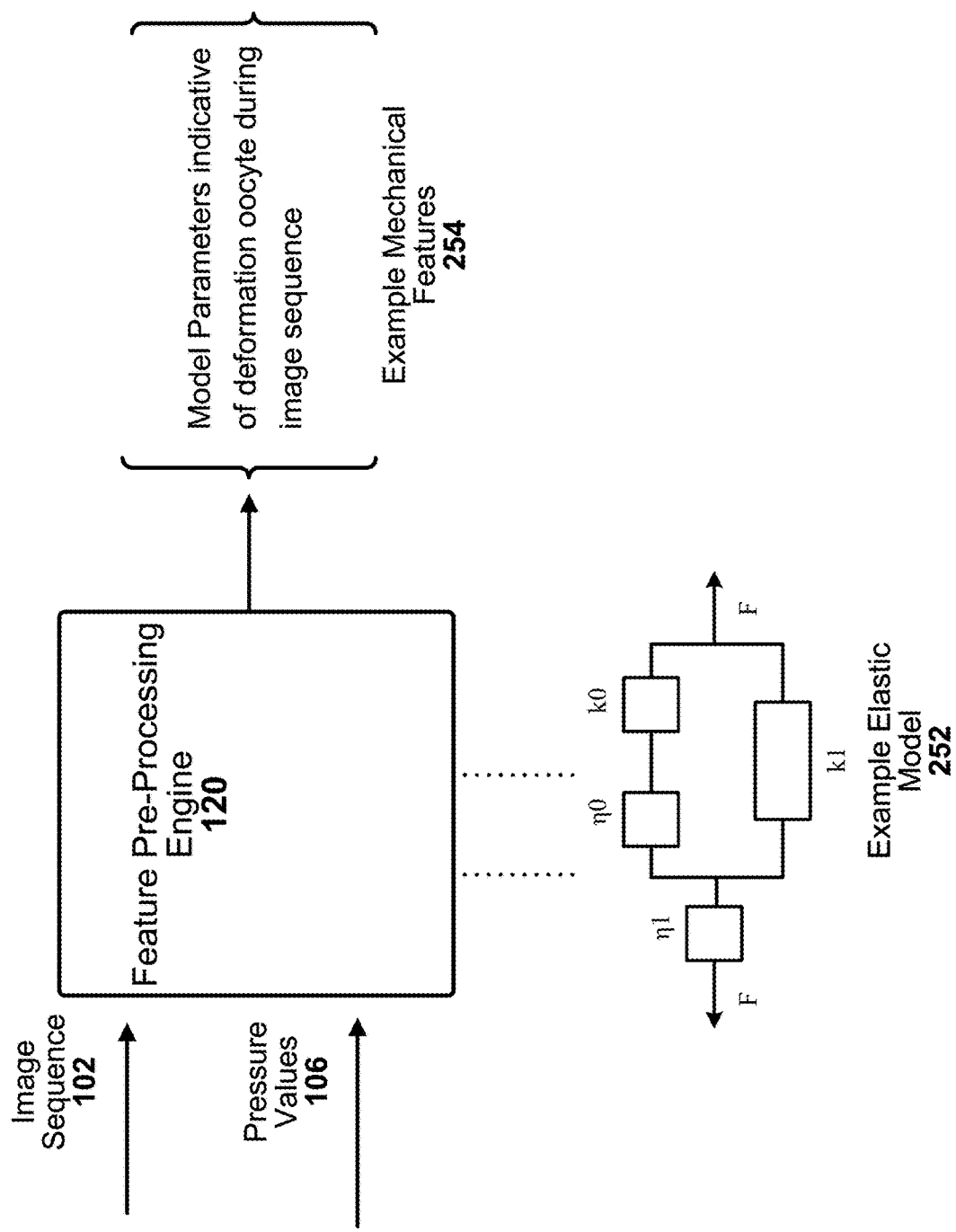
FIG. 2B illustrates mechanical features of the oocyte generated by the feature pre-processing engine of FIG. 1.

FIG. 2B illustrates mechanical features of the oocyte generated by the feature pre-processing engine 120 of FIG. 1. As shown in FIG. 2B, the feature pre-processing engine 120 receives the image sequence 102 and pressure values 106 as inputs and generates example mechanical features 254 based on an example elastic model 252. The example mechanical features 254 may be indicative of deformation or movement of the oocyte 110 during the image sequence 102.

The pressure values 106 may include forces applied on the oocyte 110 (e.g., via the above-described pressure tool 112). Specifically, the forces applied on the oocyte 110 may be calculated based on the equation (A) below. The forces may therefore be based on the pressure values and geometry information associated with the pipette.

$$\text{Force} = \text{pressure} * \text{area} \quad (A)$$
$$= \text{pressure} * psi * \left(\frac{d}{2} * \mu\right)^2 * \pi$$

where

The unit of pressure is *psi*, $psi$ = a ratio of *Pa* to *Psi*, area = $(d/2)^2 * pi$, $d$ = inner diameter of pipette $\mu$ = a ratio of *m* to $\mu m$ $\pi$ = ratio of circle's circumference to its diameter The feature pre-processing engine 120 may determine the features 254 using the above-described forces optionally in combination with the aspiration depths described in FIG. 2A.

In some embodiments, a linear elastic model, a modified linear elastic model, standard linear solid model can be used to obtain features which are indicative of the viscoelastic behavior of the oocyte 110. Example models may include a Zener model, a modified Zener model, and so on. For example, the following equation (B) may be used to fit the aspiration depths of the oocyte 110 over time to obtain mechanical features of the oocytes 110. For example, and as illustrated in FIG. 2B, a model as described above (e.g., spring-damper model) may be used with two springs and two dampers (e.g., dashpots) to model mechanical properties. The model may be fitted by minimizing the sum of squared errors between measured aspiration depth and modeled aspiration depth using an example technique (e.g., as one example, the Broyden-Fletcher-Goldfarb-Shanno algorithm). The equation (B) includes the parameters k0, k1, $\tau$, $\eta 0$ and $\eta 1$ of the example elastic model 252. These parameters may be determined by fitting the aspiration depths. In the equation (B), F0 that can indicate the force applied on the oocyte 110. For example, F0 can indicate the force associated with a particular aspiration depth (referred to as 'depth' below). In this example, the different aspiration depths associated with different times (e.g., images) may be used, along with associated respective forces, to determine the parameters. Parameters k0 and k1 model solid-like behavior of the oocyte 110 while $\eta 0$ and $\eta 1$ model liquid-like behavior of the oocyte 110. As such, the example elastic model 252 can take into account both kinds of behavior associated with the oocyte 110.

$$\text{depth}(t) = \frac{F_0}{k_1} * \left(1 - \frac{k_0}{k_0 - k_1} e^{-t/\tau}\right) - \frac{t * F_0}{\eta_1} \text{ where } \tau = \frac{\eta_0 * (k_0 + k_1)}{k_0 * k_1} \quad (B)$$

The parameters k0 and k1, can describe the "instant elongation" experienced by the oocyte 110 when the forces are applied on the oocyte 110. This instant elongation corresponds to, or is proportional to, 1/(k0+k1) and can be viewed as a measure of the "slack" in the elastic elements of the oocyte 110, or the amount of force that can be applied on the oocyte 110 before a marked resistance is exhibited. The parameter k1 can be viewed as a general measure of stiffness and may represent how tightly the proteins in the cytoplasm or zona pellucida are connected. The parameter $\eta 1$ can be viewed as a measure of how much the zona pellucida continues to deform in response to the applied forces calculated in accordance with equation (A). Like in the linear elastic solid model, after the spring elements have fully extended, $\eta 1$ is responsible for shape changes at the molecular level that keeps the oocyte 110 elongating. The parameter $\tau$ represents how fast (e.g., speed) the oocyte 110 deforms (e.g., enters into the pressure tool 112) after the initial instant elongation. $\eta 0$ can be viewed as a measure of the viscosity of the cytoplasm or the fluid in the space (e.g., PVS) between the zona pellucida and the inner cell of the oocyte 110.

In addition to use of negative pressure, other non-limiting examples of causing movement or deformation on the oocyte 110 may be used and fall within the scope of the disclosure herein. For example, positive pressure on the oocyte 110 may be used to eject the oocyte 110 or otherwise deform, hold or perturbs different portions of the oocyte 110. Example portions may include the zona pellucida, cytoplasm, or portions of the oocyte 110 near its surfaces. Other forms of forces (e.g., optical pressure) can also be applied upon the oocyte 110.

In some examples, the pressures or forces applied on the oocyte 110 are suitably tuned through the pressure tool 112 to avoid unwanted effects on the oocyte 110. For example, a pressure applied on the oocyte 110 which is too high may damage the structure of the oocyte 110 and reduce the viability of the oocyte 110. In some embodiments, the pressure applied on the oocyte 110 is between −0.01 psi to −0.5 psi (or 0.01 psi to 0.5 psi if positive pressure is applied).

In some aspects, the pressure applied on the oocyte 110 through the pressure tool 112 is adjusted based on how many days (e.g., 1, 2 or 3 days) has elapsed following fertilization. In some embodiments, the inner diameter of the pressure tool 112 is between 40 µm to 70 µm and the pressure applied may be adjusted based on the inner diameter of the pressure tool 112 to produce an appropriate level of force to be applied on the oocyte 110.

Example User Interfaces

Figure 3A:
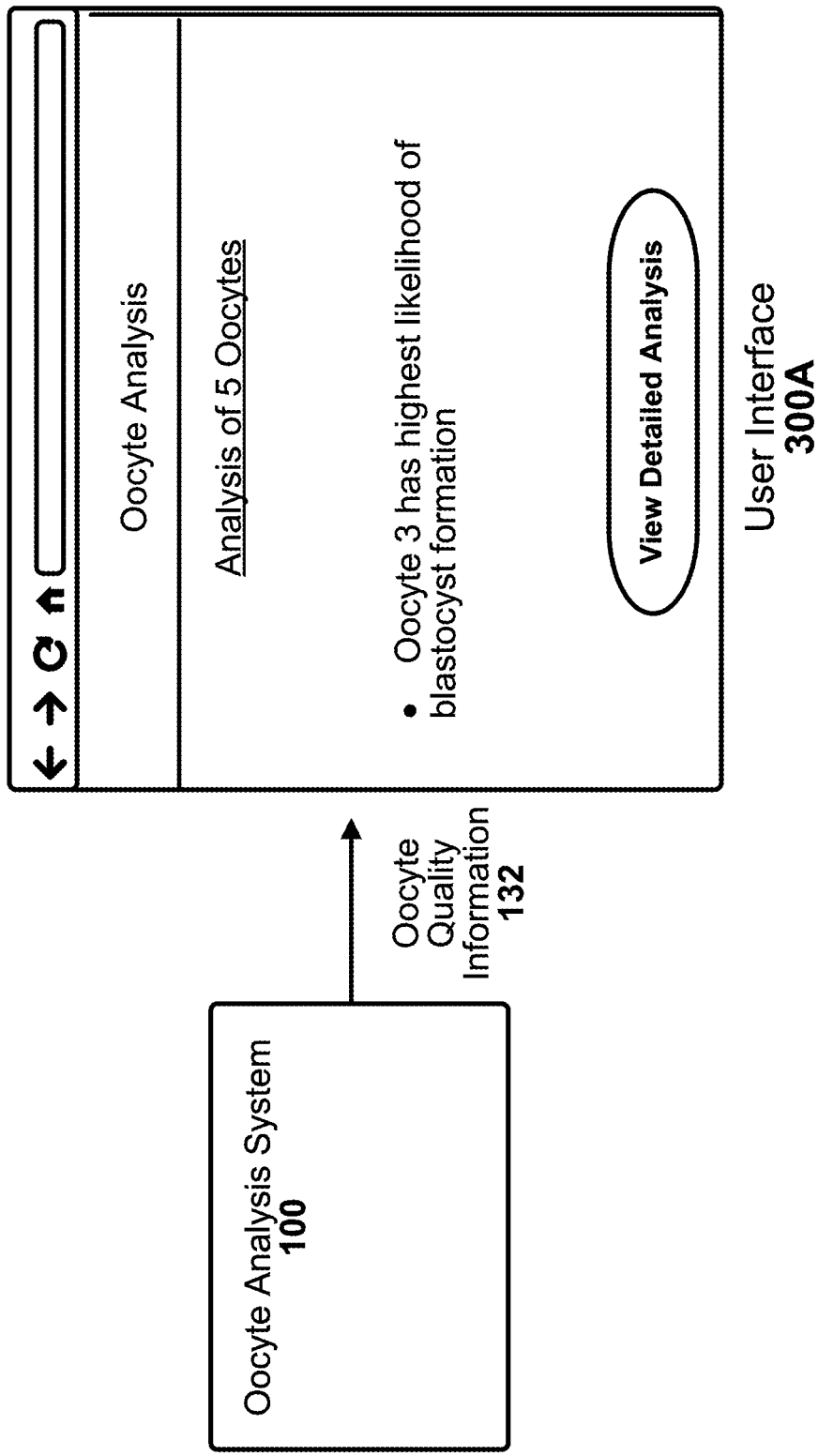
FIG. 3A illustrates an example user interface that includes example processing results.
Figure 3B:
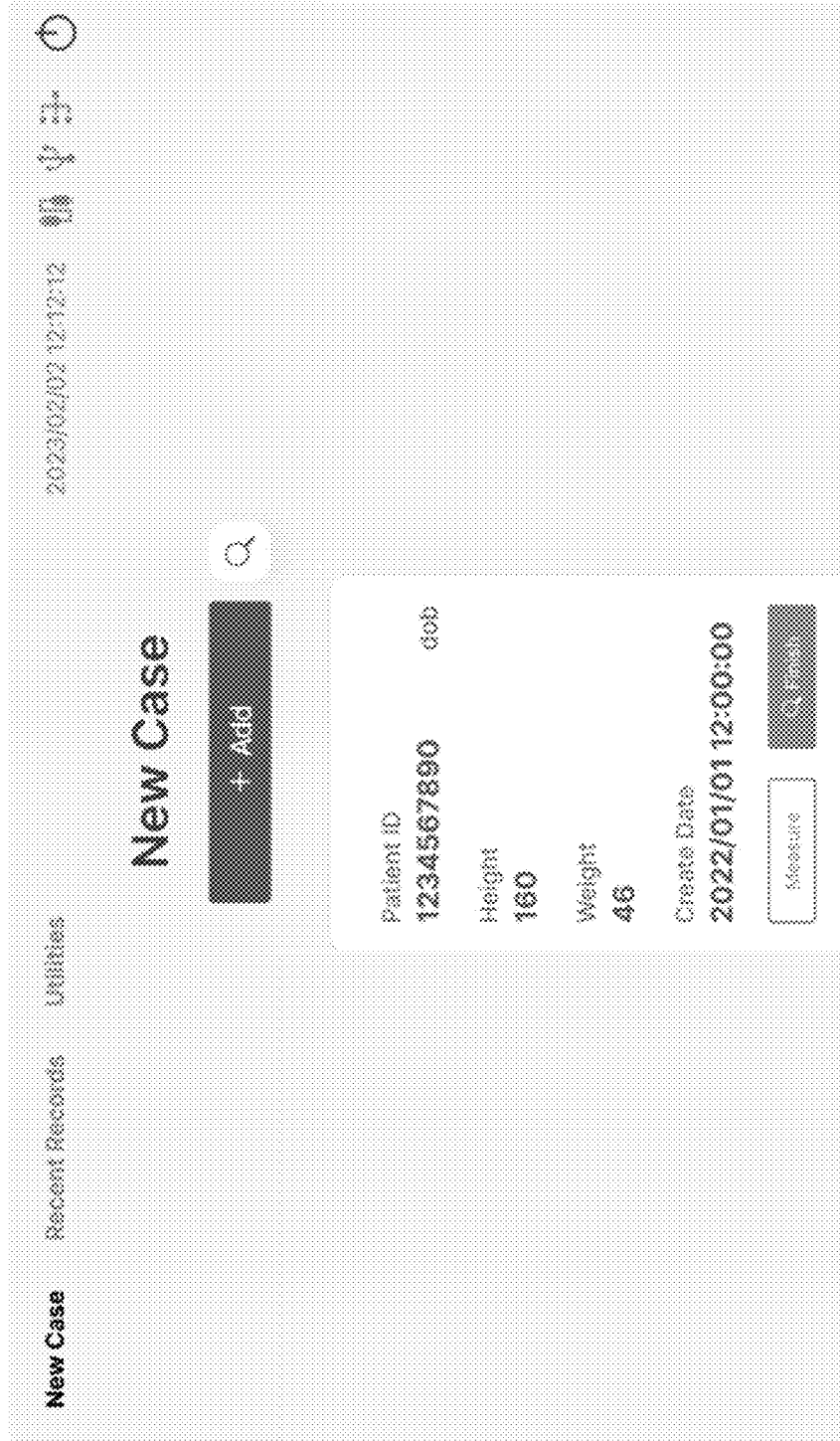
FIG. 3B illustrates an example user interface through which the example oocyte analysis system of FIG. 1 receives user inputs.
Figure 3C:
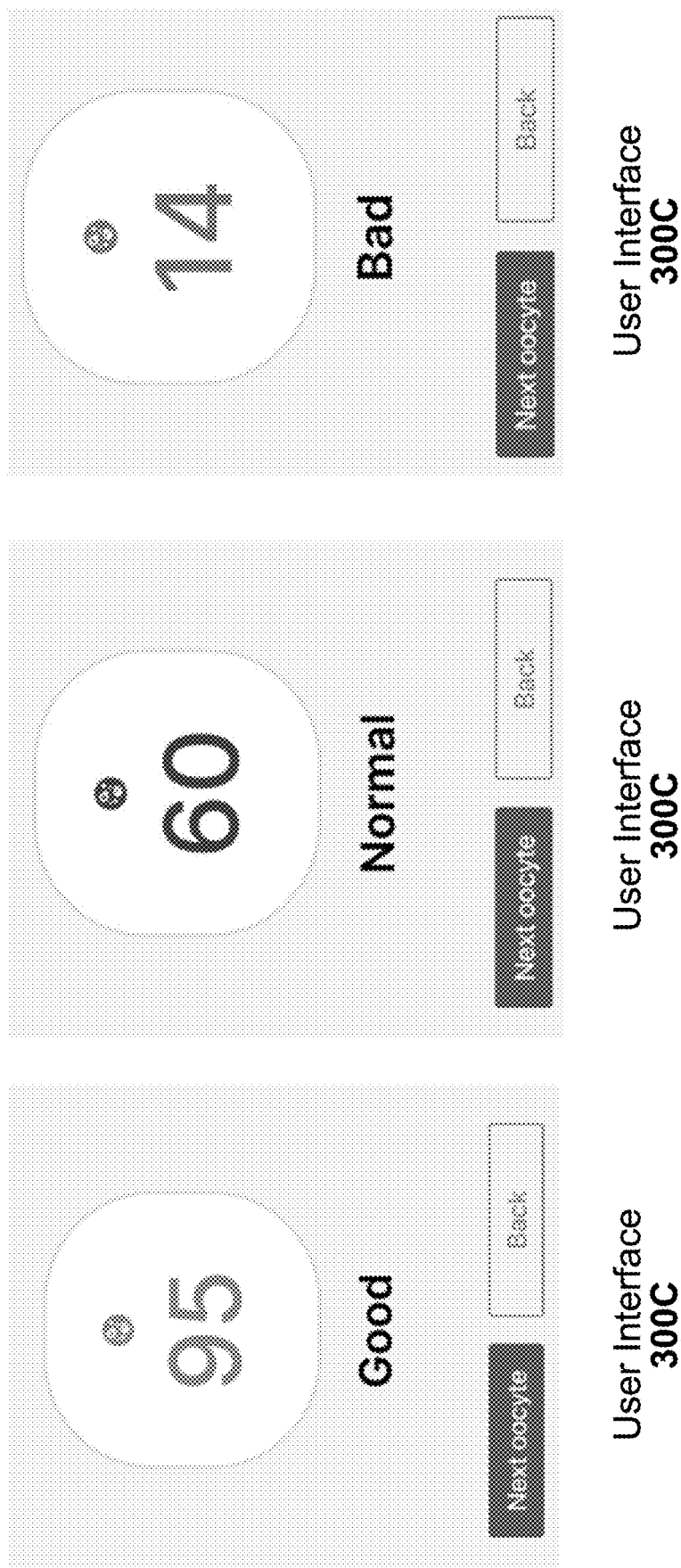
FIG. 3C illustrates another example user interface presenting processing results.

With reference to FIGS. 3A-3C, illustrative applications of the oocyte analysis system 100 of FIG. 1 will be described.

FIG. 3A illustrates an example user interface 300A that includes processing results of the example oocyte analysis system 100 of FIG. 1. As shown in FIG. 3A, the oocyte quality information 132 generated by the oocyte analysis system 100 may be presented via a user interface 300A. The user interface 300A can be presented as a web-page accessible by a browser or as a user interface of an application.

As illustrated, the user interface 300A receives oocyte quality information 132 from the system 100 described herein. The information 132 may reflect respective metrics of quality for a multitude of oocytes extracted from a patient. In the illustrated example, the user interface 300A is presenting summary information based on an analysis of 5 oocytes. The user interface 300A indicates that "oocyte 3" has the highest likelihood of blastocyst formation. This indication may be based on likelihoods of blastocyst formation as determined by a machine learning model (e.g., model 130).

The user interface 300A may respond to user input associated with viewing a detailed analysis. In some embodiments, the detailed analysis may include all, or a subset, of the features described above. The detailed analysis may include graphical representations, such as images from an image sequence, associated with oocyte 3. In some embodiments, the image sequence may be presented as a movie or animation in the user interface 300A.

In some examples, the oocyte quality information 132 can be connected with or compared to evaluation results obtained from Preimplantation Genetic Testing (PGT) or implantation conducted on the same oocyte samples. For instance, for oocytes that are indicated by the oocyte quality information 132 to be capable of blastocyst formation (e.g., "good" oocytes), PGT for aneuploidy (PGT-A) can be conducted to derive the euploidy rate of the oocytes selected by the oocyte analysis system 100. As another example, for oocytes that are indicated by the oocyte quality information 132 to be not capable of blastocyst formation (e.g., "bad" oocytes), PGT for aneuploidy (PGT-A) can also be conducted to derive the aneuploidy rate of the oocytes selected by the oocyte analysis system 100.

As another example, oocytes which are indicated by the oocyte quality information 132 to be capable of blastocyst formation (e.g., "good" oocytes, such as with likelihoods greater than a threshold) can be further evaluated after implantation. For example, this may be used to gauge the prediction capability on oocyte viability of the oocyte analysis system 100. The probability of embryo implantation can be obtained based on the "good" oocytes indicated by the oocyte analysis system 100 to evaluate the predictability of the oocyte analysis system 100. Advantageously, by connecting the different stages of evaluation on the quality of embryo, the oocyte analysis system 100 can be improved based on the evaluation results from PGT-A and implantation. For instance, a lower probability of embryo implantation may suggest that the parameters of machine learning model 130 need to be adjusted by using different subsets in the features 122 to train the machine learning model 130.

FIG. 3B illustrates an example user interface 300B that allows the example oocyte analysis system 100 of FIG. 1 to receive user inputs, such as patient information. As shown in FIG. 3B, the user interface 300B can allow users to add, edit and store patient information into the oocyte analysis system 100. As illustrated, the patient information displayed on the user interface 300B is assigned a patient ID (e.g., 1234567890). The patient ID can be used to associate a particular oocyte with a particular patient. Patient information such as height, weight and date of creation of the patient information are displayed under the patient ID. Additional patient information can be added by pressing the "+ Add" button on the center-top portion of the user interface 300B.

Although not illustrated in FIG. 3B, the user interface 300B can facilitate other interactions with the example oocyte analysis system 100. For example, other patient information such as BMI and/or age described above can also be edited and associated with a particular patient by operating the user interface 300B. The added patient information may then be utilized by the oocyte analysis system 100 to analyze quality of one or more particular oocytes. Additionally, the user interface 300B can facilitate the search of patient information of a particular patient based on Patient ID or other recorded patient information such as MII. Further, user interface 300B can allow users to edit information associated with a specific oocyte, such as the date the oocyte is received and the information about the donor (e.g., from whom the specific oocyte is retrieved) of the oocyte such as the date of birth of the donor, the height of the donor and/or the weight of the donor.

The user interface 300B may also receive user inputs that cause the example oocyte analysis system 100 to analyze a particular oocyte to generate oocyte quality information 132 about the particular oocyte. Additionally, the user interface 300B may alert a user to check or re-calibrate position of a camera that is used to capture the image sequence 102 for analyzing quality of one or more oocytes. In some embodiments, the oocyte quality information 132 generated by the example oocyte analysis system 100 may be presented to users as described below.

FIG. 3C illustrates an example user interface 300C that presents processing results of the example oocyte analysis system 100 of FIG. 1. As shown in FIG. 3C, the user interface 300C may present different oocyte quality information 132 based on the analysis performed by the oocyte analysis system 100. As illustrated in FIG. 3C, the oocyte quality information 132 is presented as a score to indicate the quality of the oocyte. Additionally, textual descriptions summarizing the quality may be presented. For example, the text may be based on quality metrics and may be selected from pre-stored textual expressions or words (e.g., normal, good, and so on) or determined using a language model (e.g., large language model).

Shown in the left is the analysis result of an oocyte that has a good score (e.g., 95), which may mean that an "usable" blastocyst is very likely to be formed by the oocyte. In contrast, shown in the right is the analysis result of an oocyte that has a poor score (e.g., 14), which may mean that no "usable" blastocyst is very likely to be formed by the oocyte. In the middle, the user interface 300C shows an analysis result of an oocyte that has a "normal" score (e.g., 60), which may mean that the oocyte is more likely to form a usable blastocyst than not.

After receiving an analysis result of a particular oocyte, the user interface 300C can allow users to view analysis result of other oocytes or prompt the example oocyte analysis system 100 to analyze quality of oocytes that have not been analyzed. Specifically, the user may view the analysis result of another oocyte by pressing the button "Next oocyte" or view analysis result of a previously analyzed oocyte by pressing the button "Back."

Example Flowcharts

Figure 4:
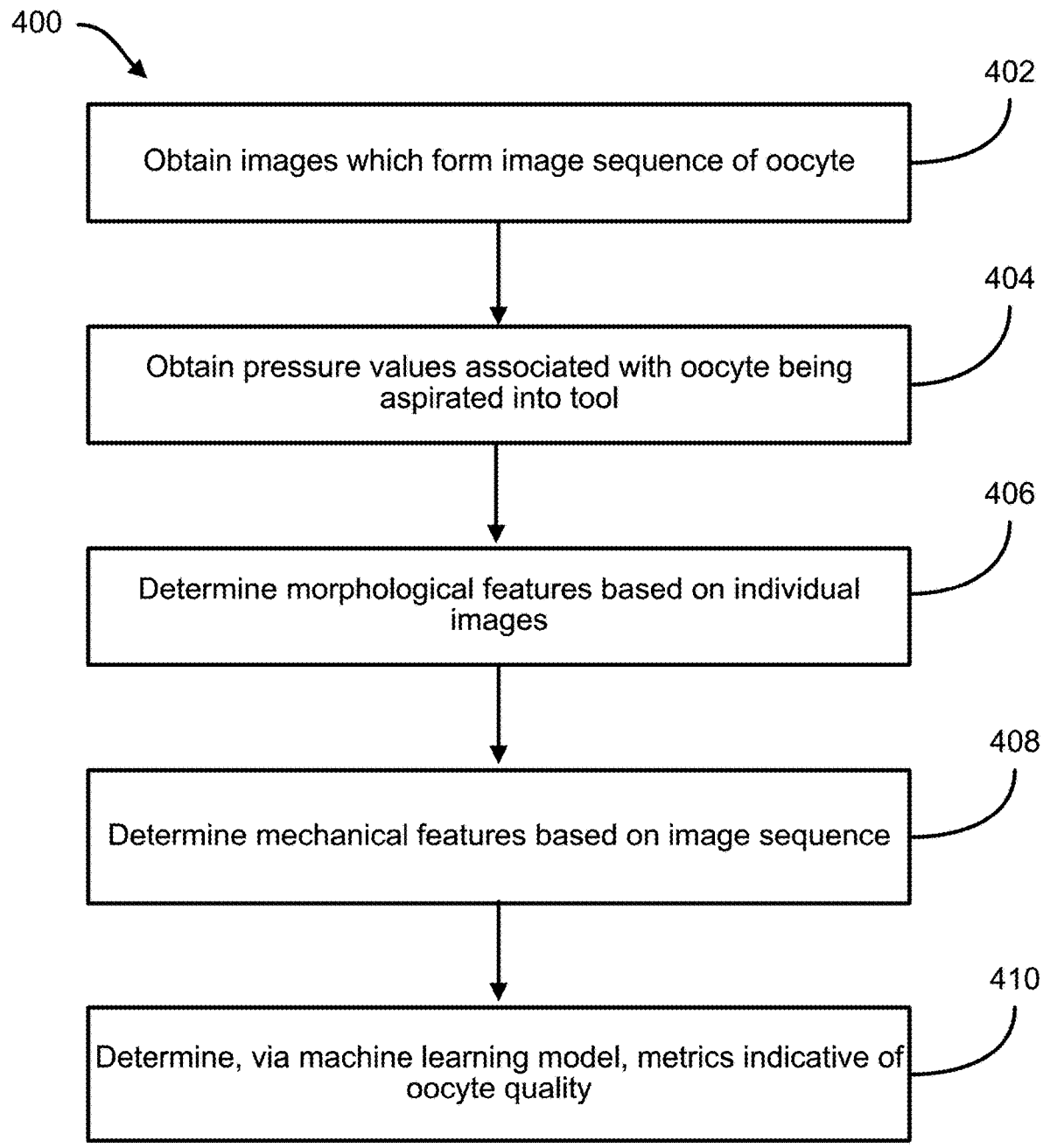
FIG. 4 is a flowchart of an example process for determining metrics indicative of the quality of an oocyte.

FIG. 4 is a flowchart of an example process 400 for determining metrics indicative of the quality of an oocyte. All or at least some parts of the process 400 may be implemented, for example, by the oocyte analysis system 100 of FIG. 1. As indicated above, the process 400 may provide for determining viability (e.g., whether there will be blastocyst formation) of the oocyte 110 without resorting to manual and subjective assessment by embryologists. As such, the process 400 may be utilized to achieve more objective, time-efficient and automated acquisition of the quality of oocyte 110.

At block 402, the system obtains images which form an image sequence of an oocyte. As discussed above, the images may be captured by microscopic cameras and depict a sequence of events showing deformation or movements of an oocyte resulted from application of forces on the oocyte by a tool (e.g., pipette).

At block 404, the system obtains pressure values associated with the oocyte being aspirated into the tool. For example, the pressure values may include pressures or forces applied to the oocyte during the process of the oocyte 110 being aspirated into the pressure tool. In some embodiments, the pressure values may be maintained as the same throughout the aspiration process. In some embodiments, the pressure values may vary in a certain manner (e.g., lower pressure followed by higher pressure applied).

At block 406, the system determines morphological features associated with the oocyte based on the obtained images that form an image sequence. Illustratively, the morphological features associated with the oocyte include aspiration depth of the oocyte, size and/or length of the cytoplasm, size and/or length of the zona pellucida and length of diameter of the tool that is used to aspirate the oocyte.

As discussed above in FIG. 2A, the morphological features can be obtained using computer vision technology and/or machine learning techniques. In some embodiments, one or more neural networks may be trained to output segmentation masks which are specific to certain of the morphological features. In this way, a size or length associated with a portion of the oocyte may be identified. In some embodiments, the segmentation may include two stages, a two-dimensional (2D) modeling followed by a three-dimensional (3D) modeling. In the 2D modeling stage, features associated with a 2D image are extracted. In the 3D modeling stage, the extracted features from a 2D image may then be concatenated to form time series data, where each of the time series data include features extracted from one 2D image in the 2D image sequence. A machine learning model (e.g., a deep learning model) may then classify the features produced by the 3D modeling stage, for example as in block 410.

At block 408, the system determines mechanical features associated with the oocyte. For example, the system determines parameters indicative of deformation or movement of the oocyte 110 during the image sequence. In this example, the parameters may relate to an elastic model as described in FIG. 2B.

At block 410, the system determines metrics indicative of oocyte quality using a machine learning model. The system provides the features, for example concatenated features determined for the images or a sequence of features determined for respective images, as input to the machine learning model. In some embodiments, the machine learning model 130 may be a support vector machine. In some embodiments, the model may be a deep learning model (e.g., a neural network). In some embodiments, a subset of the features may be provided. For example, one feature, two features, three features, 10 features, and so on may be provided.

The metrics may include at least information that is indicative of blastocyst formation of the oocyte. Additionally, one or more of the metrics may be indicative of aneuploidy and/or implantation associated with the oocyte.

In some embodiments, one or more of the metrics may indicate whether the oocyte 110 will form a "good" blastocyst, where "good" blastocyst may mean an associated Gardner Embryo/Blastocyst Grading is greater than 3 CC. Additionally and optionally, besides using the example morphological features and the example mechanical features to determine the metrics indicative of quality of the oocyte, the machine learning model may further use clinical information of the patient to determine the oocyte quality information. As mentioned in discussion with respect to FIG. 1, the clinical information may include age, BMI of the patient and/or other clinical information such as CP and MII associated with the oocyte (e.g., a development stage associated with the oocyte).

After determining the metrics indicative quality of the oocyte, process 400 may return to block 402 to determine quality information for another oocyte.

Figure 5:
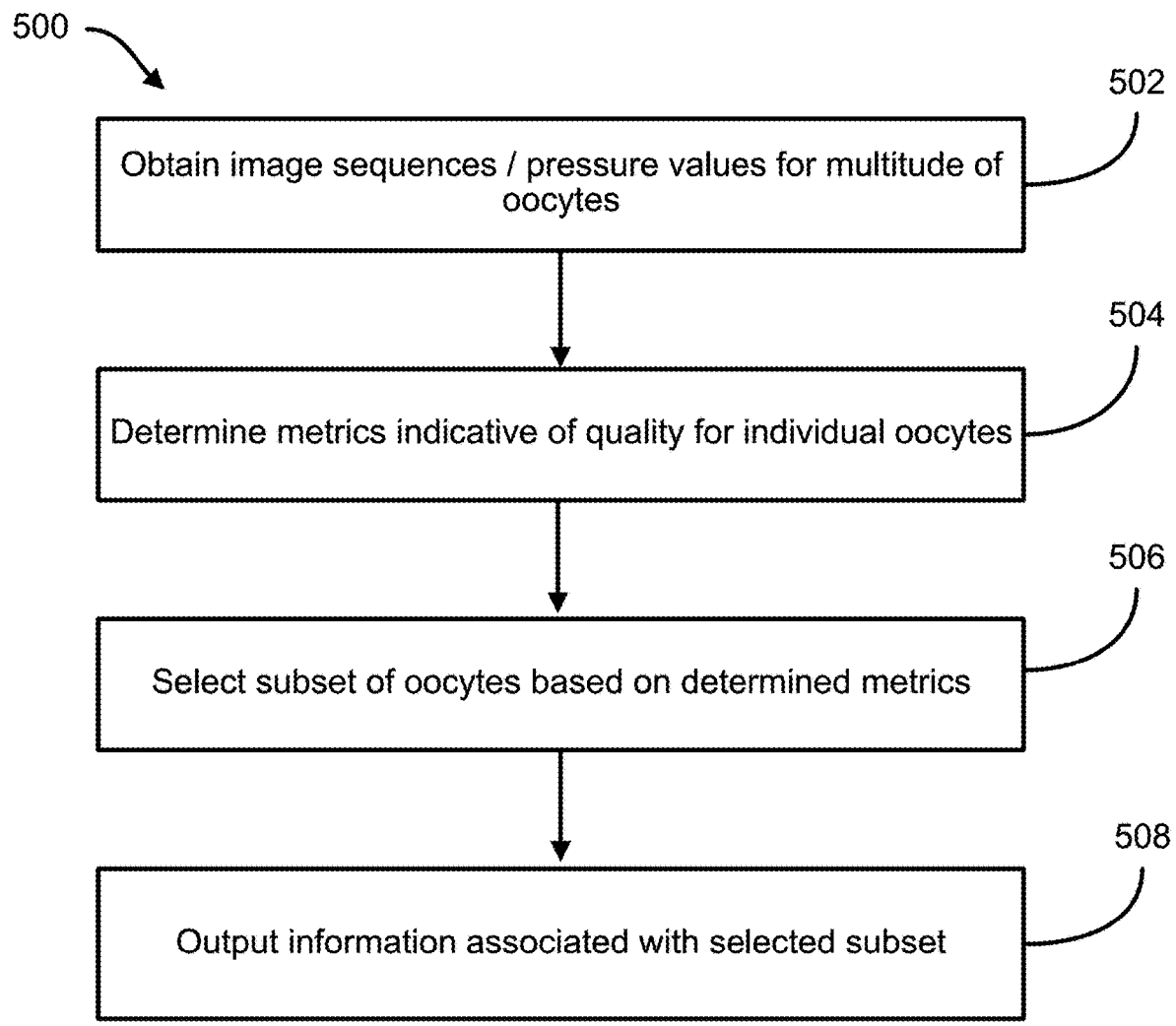
FIG. 5 is a flowchart of an example process for selecting a subset of a multitude of oocytes based on metrics indicative of quality.

FIG. 5 is a flowchart of an example process 500 for selecting a subset of a multitude of oocytes based on metrics indicative of quality. All or at least some parts of the process 500 may be implemented, for example, by the oocyte analysis system 100 of FIG. 1. The process 500 may provide for determining viability among a plurality of oocytes without resorting to time-consuming and subjective assessment by embryologists. As such, the process 500 may be utilized to achieve more objective, time-efficient and automated acquisition of the qualities of a multitude of oocytes.

At block 502, the system obtains images sequences and pressure values associated with a multitude of oocytes. As described herein, an image sequence may depict an oocyte being deformed due to application or pressure via a pressure tool.

At block 504, the system obtains metrics indicative of quality of individual oocyte in the multiple of oocytes. Determining metrics is described in more detail above and may indicate a likelihood of blastocyst formation for each of the oocytes.

At block 506, the system selects a subset of oocytes from the multitude of oocytes. For example, the system may identify a top threshold number of oocytes based on their respective likelihoods of blastocyst formation. As another example, the system may aggregate or otherwise combine the metrics for each oocyte. For this example, the system may select a top threshold number of oocytes based on the aggregated or combined metrics. As described above, the metrics may indicate blastocyst formation along with successful outcomes of later stages or metrics associated with chromosomal abnormalities (e.g., pgt-a, euploidy), and so on.

At block 508, the system outputs and/or presents information associated with the selected subset of oocytes. The information may be presented through a graphical user interface (GUI), such as the user interface 300A illustrated in FIG. 3A. The information may indicate whether a particular oocyte is likely to form blastocyst as depicted in FIGS. 3A and 3C. Additionally, other information associated with the selected subset of oocytes can be presented to a user. For example, the morphological properties, mechanical properties associated with the oocyte and/or clinical information of the patient from whom the oocyte is obtained can be presented. By implementing the process 500 using the oocyte analysis system 100, viability information associated with a multitude of oocytes can be obtained in a time-efficient manner.

Example System

Figure 6:
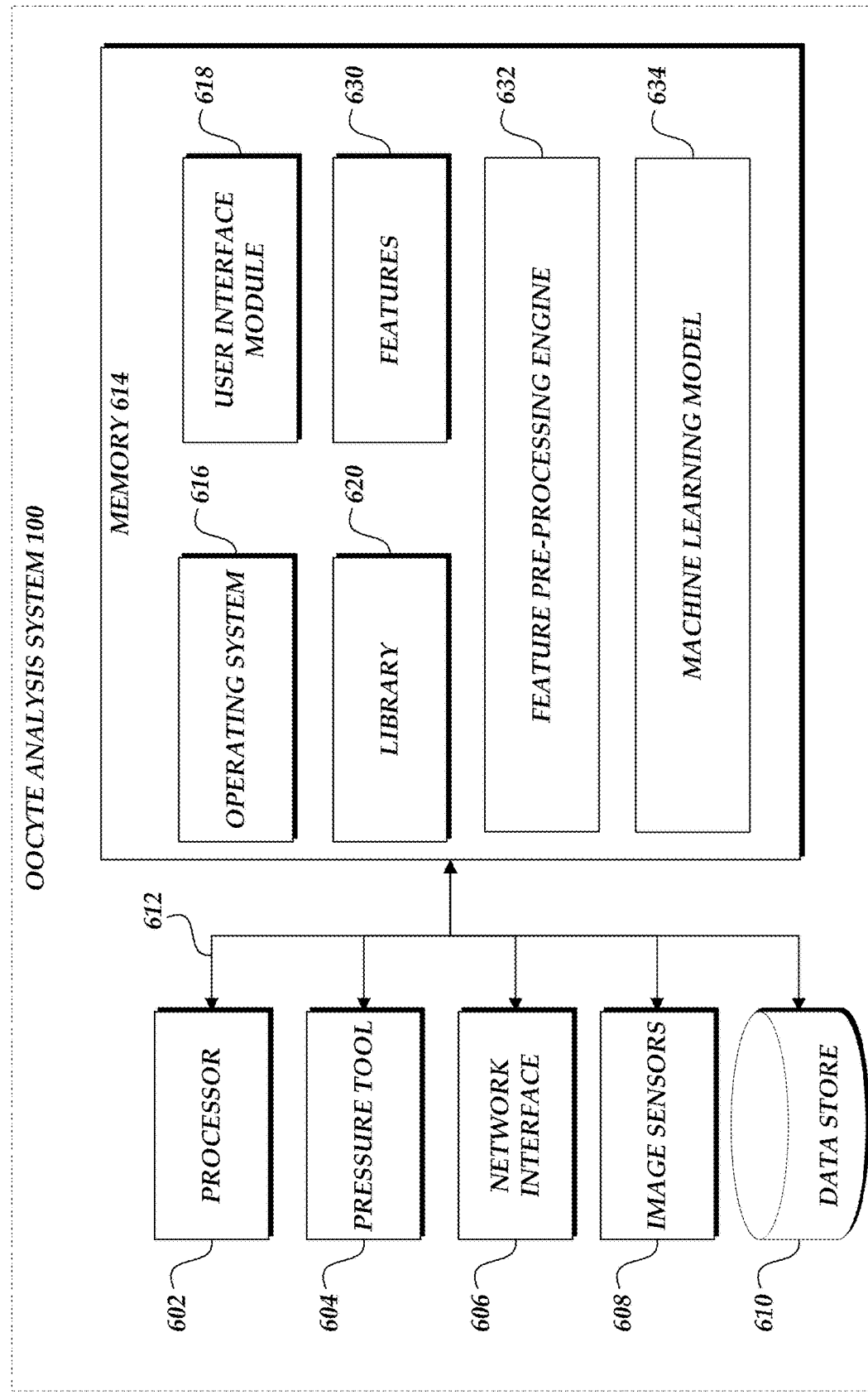
FIG. 6 illustrates a general architecture of an example oocyte analysis system in accordance with some embodiments of the present disclosure.

FIG. 6 depicts a general architecture of an example system. The system may be used, in some embodiments to perform the functionality described herein. In some embodiments, the system may be the oocyte analysis system 100, which includes an arrangement of computer hardware and software configured to implement aspects of the present disclosure. The oocyte analysis system 100 may include more (or fewer) elements than those shown in FIG. 6. It is not necessary, however, that all of these elements be shown in order to provide an enabling disclosure.

As illustrated, the oocyte analysis system 100 includes a processor 602, pressure tool 604 (e.g., the pressure tool 112 of FIG. 1), a network interface 606, image sensors 608 (e.g., one or more microscope cameras used to capture the images sequence 102 of FIG. 1) and a data store 610, all of which may communicate with one another by way of a communication bus 612. The pressure tool 112 may not be included in some embodiments and the system 100 may represent a back-end processing system. The network interface 606 may provide connectivity to one or more networks or computing systems and, as a result, may enable the oocyte analysis system 100 to receive and send information and instructions from and to other computing systems, interfaces (such as the user interface 300A of FIG. 3A) or services. In some embodiments, the oocyte analysis system 100 may be configured to process requests from other devices or modules, such as requests to analyze oocyte qualities. The data store 610 may illustratively be any non-transitory computer-readable data store, and in various embodiments may store any or all of the elements that are depicted in FIG. 6 as being loaded into a memory 614.

The processor 602 may also communicate to and from the memory 614. The memory 614 may contain computer program instructions (grouped as modules or components in some embodiments) that the processor 602 may execute in order to implement one or more embodiments. The memory 614 generally includes RAM, ROM, and/or other persistent, auxiliary, or non-transitory computer-readable media. The memory 614 may store an operating system 616 that provides computer program instructions for use by the processor 602 in the general administration and operation of the oocyte analysis system 100. The memory 614 may further store specific computer-executable instructions and other information (which may be referred to herein as "modules" or "engines") for implementing aspects of the present disclosure. For example, the memory 614 may include the feature pre-processing engine 632 and the machine learning model 634, which may implement aspects of the present disclosure as described above. The memory 614 may further store, for example, user interface module 618 that may enable presentation of information to the user interface 300A of FIG. 3A. In addition, the memory 614 can store the library 620 (e.g., for storing parameters of different types of machine learning models) and features 630 that may be extracted by the feature pre-processing engine 632. All of the modules or elements loaded into the memory 614 may also be stored in the data store 610 as various operations are performed.

It will be recognized that many of the components described in FIG. 6 are optional and that embodiments of the oocyte analysis system 100 may or may not combine components. Furthermore, components need not be distinct or discrete. Components may also be reorganized. In some embodiments, components illustrated as part of the oocyte analysis system 100 may additionally or alternatively be included in other computing devices, such that some aspects of the present disclosure may be performed by the oocyte analysis system 100 while other aspects are performed by another computing device.

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or media or device (e.g., solid state storage devices, disk drives, etc.). The various functions disclosed herein may be embodied in such program instructions, or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid-state memory chips or magnetic disks, into a different state. In some embodiments, the computer system may be a cloud-based computing system whose processing resources are shared by multiple distinct business entities or other users.

The processes described herein or illustrated in the figures of the present disclosure may begin in response to an event, such as on a predetermined or dynamically determined schedule, on demand when initiated by a user or system administrator, or in response to some other event. When such processes are initiated, a set of executable program instructions stored on one or more non-transitory computer-readable media (e.g., hard drive, flash memory, removable media, etc.) may be loaded into memory (e.g., RAM) of a server or other computing device. The executable instructions may then be executed by a hardware-based computer processor of the computing device. In some embodiments, such processes or portions thereof may be implemented on multiple computing devices and/or multiple processors, serially or in parallel.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on computer hardware, or combinations of both. Moreover, the various illustrative logical blocks and modules described in connection with the embodiments disclosed herein can be implemented or performed by a machine, such as a processor device, a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements or steps. Thus, such conditional language is not generally intended to imply that features, elements or steps are in any way required for one or more embodiments or that one or more embodiments necessarily include logic for deciding, with or without other input or prompting, whether these features, elements or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, or Z). Thus, such disjunctive language is not generally intended to, and should not, imply that certain embodiments require at least one of X, at least one of Y, and at least one of Z to each be present.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. All changes which come within the meaning and range of equivalency of the claims are to be embraced within their scope.

What is claimed is:

1. A method implemented by a system of one or more computers, the method comprising:
   obtaining a plurality of images which form an image sequence associated with a time period, the image sequence depicting an oocyte and a portion of tool applying pressure to the oocyte, wherein individual images are associated with individual pressure values applied to the oocyte at respective times of image capture;
   for each individual image of the images:
      identifying a bounding box based at least on a position of the portion of the tool in the individual image; and
      determining an aspiration depth of the oocyte into the portion of the tool using pixel intensities of at least a portion of pixels of the individual image within the bounding box;
   determining features associated with the oocyte, the features including morphological features indicative of measurements of the oocyte during the time period and mechanical features indicative of deformation of the oocyte during the time period, and the determination of the morphological features and/or the mechanical features being based on one or more of the images, aspiration depths, and pressure values; and
   determining, via a machine learning model based on input comprising at least a subset of the features, one or more metrics indicative of oocyte quality, wherein a particular metric is indicative of blastocyst formation,
   wherein the one or more metrics are configured for presentation via an interactive user interface.

2. The method of claim 1, wherein the oocyte depicted in the images is mammalian.

3. The method of claim 1, wherein the images depict the oocyte being aspirated into the portion of the tool.

4. The method of claim 1, wherein the mechanical features are indicative of elasticity of the oocyte, and wherein the mechanical features are determined based on aspiration depths of the oocyte into the portion of the tool.

5. The method of claim 4, wherein the mechanical features are indicative of viscoelastic behavior of the oocyte.

6. The method of claim 1, wherein the morphological features indicate, at least, aspiration depths of the oocyte into the portion of the tool for a respective image.

7. The method of claim 1, wherein one of the morphological features is derived through normalizing aspiration depths of the oocyte into the portion of the tool for a respective image by an inner diameter of the tool.

8. The method of claim 1, wherein the morphological features indicate first measurements associated with a cytoplasm of the oocyte and second measurements associated with a zona pellucida of the oocyte.

9. The method of claim 1, wherein the portion of the tool is a pipette, and wherein during the time period the pipette abuts the oocyte and is configured to apply pressure.

10. The method of claim 1, wherein a first image associated with a start of the time period depicts the oocyte prior to pressure being applied, and wherein a second image after the first image in the image sequence depicts the oocyte with pressure applied.

11. The method of claim 1, wherein the pressure values are selected from a pressure range applied during the time period.

12. The method of claim 1, wherein the machine learning model is a neural network.

13. The method of claim 1, further comprising:
calculating measures of pressure force applied on the oocyte based on the pressure values and geometry information associated with the portion of the tool; and
determining the mechanical features via fitting an aspiration depth curve using a linear elastic model, wherein fitting the aspiration depth curve is based on aspiration depths of the oocyte into the portion of the tool for respective images and the measures of pressure force.

14. The method of claim 1, wherein the input further comprises clinical information associated with the oocyte, the clinical information including a developmental stage associated with the oocyte.

15. The method of claim 1, wherein determining the aspiration depth of the oocyte into the portion of the tool comprises performing at least one arithmetic operation on the pixel intensities of at least the portion of pixels within the bounding box of the individual image.

16. The method of claim 15, wherein the at least one arithmetic operation comprises summing, along a first direction with reference to the bounding box, the pixel intensities of at least the portion of pixels within the bounding box of the individual image to generate a pixel intensity curve.

17. The method of claim 16, wherein the at least one arithmetic operation comprises calculating a derivative of the pixel intensity curve to generate a derivative curve.

18. A system comprising one or more processors and non-transitory computer storage media storing instructions that when executed by the one or more processors, cause the one or more processors to:
obtain a plurality of images which form an image sequence associated with a time period, the image sequence depicting an oocyte and a portion of tool applying pressure to the oocyte, wherein individual images are associated with individual pressure values applied to the oocyte at respective times of image capture;
for each individual image of the images:
identify a bounding box based at least on a position of the portion of the tool in the individual image; and
determine an aspiration depth of the oocyte into the portion of the tool using pixel intensities of at least a portion of pixels of the individual image within the bounding box;
determine features associated with the oocyte, the features including morphological features indicative of measurements of the oocyte during the time period and mechanical features indicative of deformation of the oocyte during the time period, and the determination of the morphological features and/or the mechanical features being based on one or more of the images, aspiration depths, and pressure values; and
determine, via a machine learning model based on input comprising at least a subset of the features, one or more metrics indicative of oocyte quality, wherein a particular metric is indicative of blastocyst formation,
wherein the one or more metrics are configured for presentation via an interactive user interface.

19. The system of claim 18, wherein the mechanical features are indicative of elasticity of the oocyte, and wherein the mechanical features is determined based on aspiration depths of the oocyte into the portion of the tool.

20. The system of claim 19, wherein the mechanical features are indicative of viscoelastic behavior of the oocyte.

21. The system of claim 18, wherein the morphological features indicate, at least, aspiration depths of the oocyte into the portion of the tool for a respective image.

22. The system of claim 18, wherein the morphological features indicate first measurements associated with a cytoplasm of the oocyte and second measurements associated with a zona pellucida of the oocyte.

23. The system of claim 18, wherein the pressure values are selected from a pressure range applied during the time period.

24. The system of claim 18, wherein the instructions further cause the one or more processors to:
calculate measures of pressure force applied on the oocyte based on the pressure values and geometry information associated with the portion of the tool; and
determine the mechanical features via fitting an aspiration depth curve using a linear elastic model, wherein fitting the aspiration depth curve is based on aspiration depths of the oocyte into the portion of the tool for respective images and the measures of pressure force.

25. The system of claim 18, wherein the input further comprises clinical information associated with the oocyte, the clinical information including a developmental stage associated with the oocyte.

26. A method implemented by a system of one or more computers, the method comprising:
obtaining a plurality of image sequences depicting respective oocytes, wherein individual image sequences include images depict an individual oocyte and a portion of a tool applying pressure to the oocyte, and wherein pressure values associated with respective images included in the individual image sequences are obtained;
for each individual image of the images with associated pressure values:
identifying a bounding box based at least on a position of the portion of the tool in the individual image; and
determining an aspiration depth of the oocyte into the portion of the tool using pixel intensities of at least a portion of pixels of the individual image within the bounding box;
determining, via a machine learning model, one or more metrics indicative of oocyte quality for each of the oocytes, wherein a particular metric is indicative of blastocyst formation, wherein input to the machine learning model for each oocyte includes morphological features indicative of measurements of the oocyte and mechanical features indicative of deformation of the oocyte during a time in which pressure is applied to the oocyte, and wherein the morphological features and/or the mechanical features are determined based on one or more of the images, aspiration depths and pressure values; and outputting information indicating selection of one or more oocytes, the selection being based on the metrics.

27. The method of claim 26, wherein the images depict the oocyte being aspirated into the portion of the tool.

28. The method of claim 26, wherein the mechanical features are indicative of elasticity of the oocyte, and wherein the mechanical features are determined based on aspiration depths of the oocyte into the portion of the tool.

29. The method of claim 26, wherein the morphological features indicate first measurements associated with a cytoplasm of the oocyte and second measurements associated with a zona pellucida of the oocyte.

30. The method of claim 26, wherein the information indicating selection is output via an interactive user interface, and wherein the interactive user interface:
presents a graphical depiction of the one or more oocytes,
responds to user input selecting a particular oocyte of the one or more oocytes, and
presents detailed information associated with the particular oocyte.

31. The method of claim 26, wherein the information indicating selection is output via an interactive user interface, and wherein the interactive user interface presents individual textual descriptions which summarize individual oocytes of the one or more oocytes.

\* \* \* \* \*